US006836906B2

(12) United States Patent
Holmes

(10) Patent No.: US 6,836,906 B2
(45) Date of Patent: Jan. 4, 2005

(54) EYE PROTECTION DEVICE

(75) Inventor: Richard James Holmes, Salisbury (GB)

(73) Assignee: The Secretary of State for Defence in Her Britannic Majesty's Government of the United Kingdom of Great Britain and Northern Ireland, Salisbury (GB)

( * ) Notice: Subject to any disclaimer, the term of this patent is extended or adjusted under 35 U.S.C. 154(b) by 0 days.

(21) Appl. No.: 10/398,878

(22) PCT Filed: Oct. 9, 2001

(86) PCT No.: PCT/GB01/04456
§ 371 (c)(1),
(2), (4) Date: Apr. 11, 2003

(87) PCT Pub. No.: WO02/30227
PCT Pub. Date: Apr. 18, 2002

(65) Prior Publication Data
US 2004/0031089 A1 Feb. 19, 2004

(51) Int. Cl.[7] .................................................. A42C 5/04
(52) U.S. Cl. ........................ 2/171.3; 2/6.1; 128/200.28; 454/188
(58) Field of Search .......................... 2/436, 437, 428, 2/9, 410, 6.2, 6.1, 6.3, 6.4, 6.5, 171.3; 128/200.28, 201.15, 201.25, 201.22, 201.23, 206.24; 454/188, 189

(56) References Cited

U.S. PATENT DOCUMENTS

| 735,959 | A | * | 8/1903 | Folkmar | 128/200.28 |
|---|---|---|---|---|---|
| 1,410,926 | A | * | 3/1922 | Knoblock | 128/201.15 |
| 2,032,101 | A | * | 2/1936 | Sullivan | 128/200.28 |
| 2,447,433 | A | * | 8/1948 | Schroeder | 128/201.15 |
| 2,507,705 | A | * | 5/1950 | Gaddini | 128/205.25 |
| 3,239,843 | A | * | 3/1966 | Lobelle | 2/6.4 |
| 3,293,659 | A | * | 12/1966 | Shepard | 128/201.15 |
| 3,566,409 | A | * | 3/1971 | Hopper | 2/414 |
| 3,584,314 | A | * | 6/1971 | Hobson | 128/205.25 |
| 3,657,740 | A |  | 4/1972 | Cialone |  |
| 3,736,927 | A | * | 6/1973 | Misaqi | 128/201.25 |
| 3,825,953 | A |  | 7/1974 | Hunter |  |
| 3,881,478 | A | * | 5/1975 | Rosendahl et al. | 128/200.28 |
| 4,150,443 | A |  | 4/1979 | McNeilly |  |
| 4,352,353 | A | * | 10/1982 | Bolton et al. | 128/201.24 |
| 4,502,480 | A |  | 3/1985 | Yamamoto |  |
| 5,050,240 | A |  | 9/1991 | Sayre |  |
| 5,146,757 | A |  | 9/1992 | Dearing |  |
| 5,177,816 | A | * | 1/1993 | Schmidt et al. | 2/424 |
| 5,283,914 | A | * | 2/1994 | James | 2/424 |
| 5,878,742 | A | * | 3/1999 | Figueredo et al. | 128/201.24 |
| RE36,242 | E | * | 6/1999 | Apisdorf | 2/171.3 |
| 5,921,467 | A |  | 7/1999 | Larson |  |

FOREIGN PATENT DOCUMENTS

| EP | 0651228 | 5/1995 |
|---|---|---|
| EP | 0967453 | 12/1999 |
| FR | 2109042 | * 5/1972 |
| WO | WO 94/24894 | 11/1994 |

* cited by examiner

Primary Examiner—Rodney M. Lindsey
(74) Attorney, Agent, or Firm—Dean W. Russell; Kilpatrick Stockton LLP

(57) ABSTRACT

With reference to FIG. (2), a helmet (2) for an aircraft crew member (1) is provided with a device (10) for forming an eye-shielding curtain (11) of air in front of the crew members eyes. The air exhausts to the ambient atmosphere (9) by way of an escape path (12) beneath the lower edge of the visor (4), as indicated by arrow (13).

19 Claims, 2 Drawing Sheets

Figure 2:
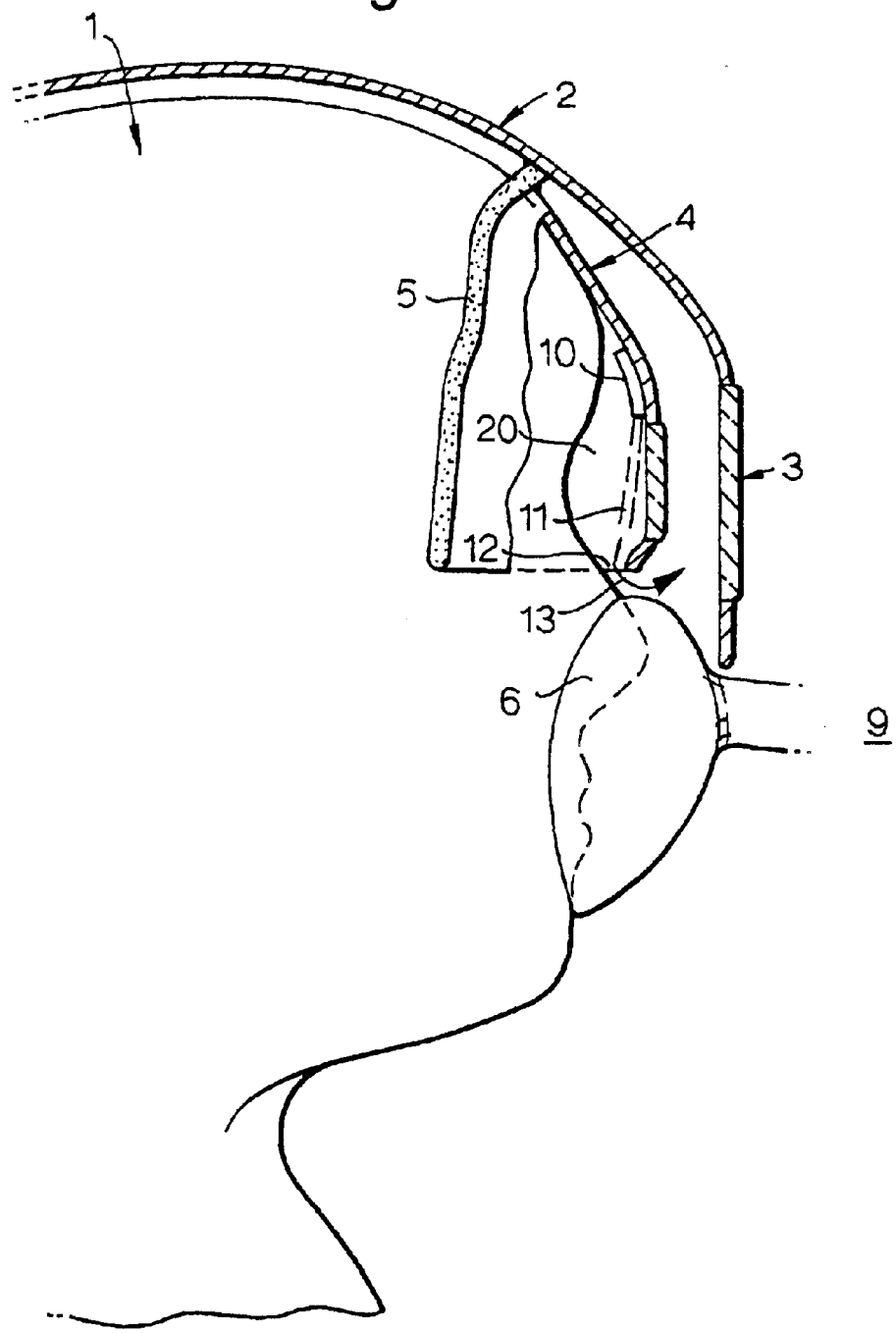

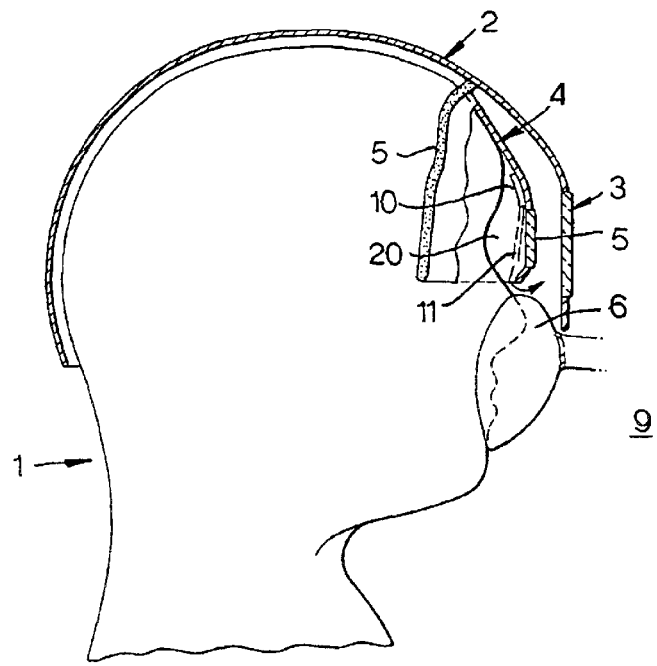
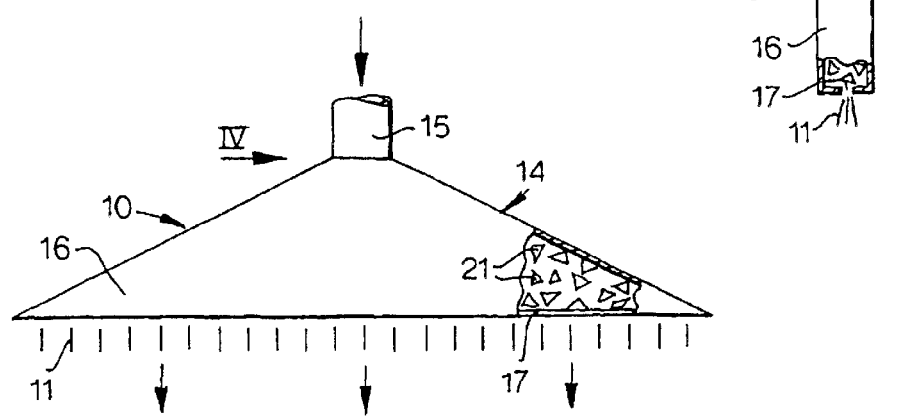

EYE PROTECTION DEVICE

CROSS REFERENCE TO RELATED APPLICATIONS

This application claims priority to Great Britain Application No. 0024896.3 filed on Oct. 11, 2000 and is the U.S. national phase of International Application No. PCT/GB01/04456 filed on Oct. 9, 2001 published in English as International Publication No. WO 02/30227 A1 on Apr. 18, 2002, the entire contents of which are hereby incorporated by reference.

This invention relates to eye protection devices, and particularly, but not exclusively, relates to eye protection devices for aircraft crew members.

In certain operational conditions, aircraft crew members are sometimes troubled by ambient atmospheres which can irritate the eyes. These effects can be due to chemical warfare agents or other hazards, and some of these hazards can affect flight safety or the ability to undertake delicate tasks.

The present invention seeks to at least alleviate this problem.

According to the present invention, an eye protection device comprises means for forming an eye-shielding curtain of air in front of the eyes.

The invention has many applications and particularly, but not exclusively, provides an embodiment comprising a helmet incorporating such an eye protection device. The helmet may comprise an aircraft crew member's helmet.

An embodiment of the invention will now be described by way of example only, with reference to the accompanying drawings, wherein:

FIG. 1 is a side view, partly in section of an aircraft crew wearing a helmet incorporating an eye protection device, FIG. 2 is an enlargement of part of FIG. 1 and illustrates further detail, FIG. 3 is front view of the eye protection device, and FIG. 4 is an end view of the device, looking in the direction of arrow IV of FIG. 3.

With reference to the figures, an aircraft crew member 1 is shown wearing a helmet 2 which fits closely to the head and is held firmly in place, eg, using a strap FR-A-2 109 042 discloses protection equipment, especially a helmet, for a car driver comprising on the inside a perforated frontal ramp connected to a pressurised fluid supply tubing system. In the event of an accident the fluid system is released, cools and forms a protection curtain in front of the driver's face. The present invention seeks to improve upon this system for use to alleviate the present problem.

What is claimed is:

1. An eye-protection device for forming an eye-shielding curtain of air in front of the eyes, wherein the device comprises a casing having an air inlet, a divergent portion which serves as an air diffuser and an air discharge slot and in which the divergent portion houses a plurality of particles which define tortuous paths for out-flowing air.

2. An eye-protection device as claimed in claim 1 wherein the air discharge slot is defined by a divergent air outlet.

3. An eye-protection device as claimed in claim 1 wherein the particles are of generally triangular shape.

4. An eye-protection device as claimed in claim 1 wherein the eye-shielding curtain of air is slightly pressurized.

5. Use of eye-protection device as claimed in claim 1 to form an eye-shielding curtain of slightly pressurized clean air discharged downwardly across, but not into, the crew member's eyes.

6. A helmet for use by a wearer having a brow and eyes, the helmet comprising (a) an eye-protection device comprising means for forming an eye-shielding curtain of air in front of the eyes, wherein the device comprises a casing having an air inlet, a divergent portion which serves as an air diffuser and an air discharge slot and (b) a curved visor disposed in front of the wearer's eyes and the eye-protection device and having vertical sides, the visor being provided with a peripheral seal extending along the brow and vertical sides to define a bottom opening providing a curtain air escape path.

7. A helmet as claimed in claim 6 wherein the eye-protection device is curved to conform with the visor.

8. A helmet as claimed in claim 6 wherein there is no seal along the bottom edge of the visor.

9. A helmet as claimed in claim 6 comprising a flexible oronasal mask which does not provide an airtight seal with the visor.

10. A helmet as claimed in claim 6 comprising a further outer visor.

11. A helmet as claimed in claim 6 comprising an aircraft crew member's helmet.

12. An eye-protection device for forming an eye-shielding curtain of air in front of the eyes of a wearer also having a brow and temples, said device comprising a visor and an air diffusing casing disposed behind the visor, and in which (a) the casing comprises an air inlet portion, a divergent portion and an air discharge slot and (b) the visor (i) has a lower edge and (ii) carries a soft rubber lip giving a peripheral seal along the brow and temples but leaving an opening beneath its lower edge and the wearer for the escape of air.

13. A device according to claim 12 which the divergent portion houses a material providing for a tortuous airflow therethrough.

14. A device according to claim 13 in which the material comprises particles of generally triangular shape.

15. A device according to claim 13 in which the material comprises bubble pack.

16. A device according to claim 12 which the width of the opening beneath the lower edge of the visor is approximately 4.5 mm and the width of the discharge slot is approximately 2.5 mm.

17. A helmet incorporating the device of claim 12.

18. A device according to claim 12 in which the wearer is a member of an aircrew.

19. A device according to claim 12 useful for protecting against chemical warfare agents.

* * * * *